(12) United States Patent
Rodriguez et al.

(10) Patent No.: US 12,274,641 B2
(45) Date of Patent: Apr. 15, 2025

(54) METHODS AND APPARATUS FOR CONVENIENT AND ACCURATE PLACEMENT OF EYE DROPS

(71) Applicant: Papeltec Overseas, Inc., Atlantic Beach, FL (US)

(72) Inventors: Peter Rodriguez, Jacksonville, FL (US); Jason A. Rodriguez, Jacksonville, FL (US); Craig Austin, Jacksonville, FL (US)

(73) Assignee: Papeltec Overseas, Inc., Atlantic Beach, FL (US)

( * ) Notice: Subject to any disclaimer, the term of this patent is extended or adjusted under 35 U.S.C. 154(b) by 0 days.

(21) Appl. No.: 18/628,726

(22) Filed: Apr. 6, 2024

(65) Prior Publication Data
US 2024/0245552 A1    Jul. 25, 2024

Related U.S. Application Data

(63) Continuation-in-part of application No. 18/129,884, filed on Apr. 2, 2023, now abandoned.

(60) Provisional application No. 63/326,891, filed on Apr. 3, 2022.

(51) Int. Cl.
*A61F 9/00* (2006.01)
(52) U.S. Cl.
CPC .................... *A61F 9/0026* (2013.01)
(58) Field of Classification Search
CPC ..... A61F 9/0026; A61F 9/0008; G02C 5/008; G02C 2200/10
USPC .............................. 351/41, 90, 102, 103, 110
See application file for complete search history.

(56) References Cited

U.S. PATENT DOCUMENTS

| | | | | |
|---|---|---|---|---|
| 4,468,103 A | * | 8/1984 | Meckler | G02C 11/00 351/158 |
| 4,828,355 A | * | 5/1989 | Lipson | G02C 5/00 351/158 |
| 4,859,048 A | * | 8/1989 | Jannard | G02C 7/02 351/44 |

(Continued)

FOREIGN PATENT DOCUMENTS

| | | |
|---|---|---|
| CN | 210728007 U | 6/2020 |
| CN | 215020347 U | 12/2021 |
| DE | 2447872 B1 | 7/1975 |

OTHER PUBLICATIONS

International Search Report and Written Opinion issued in correlated application PCT/US2023/017237 on Oct. 17, 2023.

*Primary Examiner* — Sarah Al Hashimi
*Assistant Examiner* — Arjuna P Chatrathi
(74) *Attorney, Agent, or Firm* — Tracnik Law PLLC; Joseph P. Kincart

(57) ABSTRACT

The present disclosure provides methods and apparatus for administration of ophthalmic treatments into a patient's eye. Apparatus may include a wire form with a horizontal upper frame, temples that rest on or hook over the ears, nose pads, and semi-circular receivers to accept the tip of an eye drop-dispenser bottle. In some examples, distance sensing apparatus and signaling capabilities may be present to support the administration of ophthalmic treatments. In some examples, the apparatus may be enhanced for the purposes of aiding the application of eyedrops by a deep upper horizontal frame that rests on the forehead to prevent the apparatus, and thereby the eye dropper bottle, from approaching the eye too closely.

18 Claims, 15 Drawing Sheets

(56) References Cited

U.S. PATENT DOCUMENTS

| | | | |
|---|---|---|---|
| 5,255,024 A | 10/1993 | Jensen | |
| 7,559,647 B2 * | 7/2009 | Curiel | G02C 3/003 |
| | | | 351/158 |
| 2004/0204674 A1 * | 10/2004 | Anderson | A61F 9/0008 |
| | | | 604/66 |
| 2004/0207803 A1 * | 10/2004 | Paukovits, Jr. | G02C 11/00 |
| | | | 351/47 |
| 2010/0160872 A1 | 6/2010 | Harrison | |
| 2011/0071481 A1 | 3/2011 | Chen | |
| 2011/0098664 A1 * | 4/2011 | Rehkemper | A61F 9/0026 |
| | | | 604/300 |
| 2013/0030393 A1 * | 1/2013 | Bogdan | A61F 9/0026 |
| | | | 351/59 |
| 2016/0228292 A1 | 8/2016 | Michalos | |
| 2018/0335642 A1 * | 11/2018 | Kruse | B29D 11/00432 |
| 2019/0290486 A1 * | 9/2019 | Lipchak | A61F 9/0026 |
| 2020/0285070 A1 * | 9/2020 | Neuman | B21F 45/002 |
| 2021/0353458 A1 * | 11/2021 | Stowe | A61F 9/0017 |
| 2022/0039998 A1 * | 2/2022 | Ivri | A61F 9/0008 |

\* cited by examiner

1000

```
┌─────────────────────────────────────────────────────────────────────┐
│ PLACE AN APPARATUS FOR ADMINISTRATION OF AN OPHTHALMIC MEDICAMENT INTO │
│           A PATIENT'S EYE UPON A HEAD OF THE PATIENT,                │
│                              1002                                    │
└─────────────────────────────────────────────────────────────────────┘
                                  ↓
┌─────────────────────────────────────────────────────────────────────┐
│     SUPPORTING THE OPHTHALMIC MEDICAMENT CONTAINER IN A POSITION FOR │
│                            DISPENSING                                │
│                              1004                                    │
└─────────────────────────────────────────────────────────────────────┘
                                  ↓
┌─────────────────────────────────────────────────────────────────────┐
│   WITH THE GUIDE FEATURES DIRECTING THE MEDICAMENT CONTAINER TOWARDS │
│                         THE FIRST RECEIVER                           │
│                              1006                                    │
└─────────────────────────────────────────────────────────────────────┘
                                  ↓
┌─────────────────────────────────────────────────────────────────────┐
│         MOVE THE RECEPTACLE INTO ENGAGEMENT WITH THE FIRST RECEIVER  │
│                              1008                                    │
└─────────────────────────────────────────────────────────────────────┘
                                  ↓
┌─────────────────────────────────────────────────────────────────────┐
│   DISPENSE THE OPHTHALMIC MEDICAMENT FROM THE RECEPTACLE INTO THE    │
│                           PATIENT'S EYE                              │
│                              1010                                    │
└─────────────────────────────────────────────────────────────────────┘
                                  ↓
┌─────────────────────────────────────────────────────────────────────┐
│                    FORMING THE FRAME WITH A WIRE                     │
│                              1012                                    │
└─────────────────────────────────────────────────────────────────────┘
                                  ↓
┌─────────────────────────────────────────────────────────────────────┐
│   FORMING THE FRAME AND A FIRST PLASTIC SHAPED LENS PIECES           │
│              TO SUPPORT THE MEDICAMENT CONTAINER                     │
│                              1014                                    │
└─────────────────────────────────────────────────────────────────────┘
```

MOLD A PLASTIC MATERIAL INTO THE SHAPE SUITABLE FOR BRIDGING A BROW, EYES, AND NOSE OF A PATIENT

1102

USING AN INSERT PIECE, LOCATING A DISPENSER IN A POSITION FOR DISPENSING OPHTHALMIC MEDICAMENT INTO THE PATIENT'S EYE

1104

201 – semi-circular receivers

202 - V-shaped grooves 1201 specialized insert 1201 specialized insert
1300 signaling function
1310 energy source
1320 Proximity sensing
1330 Controller
1340 Communication 1410 — Obtain a medicament dispensing support structure with a distance sensing means 1420 — Interface a medicament storage element with the dispensing support structure.

1430 — Position the medicament dispensing support structure and the distance sensing means upon the head of the user 1440 — Optionally, initialize the distance sensing means.

1450 — Flex the frame of the medicament dispensing support structure to move the distance sensing means towards or away from the user's eye surface 1460 — Signal or electronically communicate from the apparatus when a distance within a desired range is sensed 1470 — Dispense the medicament

FIG. 14

METHODS AND APPARATUS FOR CONVENIENT AND ACCURATE PLACEMENT OF EYE DROPS

CROSS REFERENCE TO RELATED APPLICATIONS

This application claims priority to the pending U.S. application Ser. No. 18/129,884, filed Apr. 2, 2023 and entitled METHODS AND APPARATUS FOR CONVENIENT AND ACCURATE PLACEMENT OF EYE DROPS, which in turn claims the benefit of U.S. Provisional Application No. 63/326,891, filed Apr. 3, 2022 and entitled METHODS AND APPARATUS FOR CONVENIENT AND ACCURATE PLACEMENT OF EYE DROPS, the entire disclosure of each of which is incorporated herein by reference.

FIELD OF THE DISCLOSURE

The present disclosure relates to methods and apparatus to support convenient and accurate placement of medicaments, or other beneficial liquids, gels, or powders, into a patient's eye. The apparatus may include designs of medicament containers and/or support structure for holding a medicament dispenser in a fixed position or in a supported position. The apparatus and methods may include designs of holding features that also incorporate distance sensing between the patient's eye and a medicament container and feedback to the user.

BACKGROUND OF THE DISCLOSURE

Many people are prescribed ophthalmic solutions or choose to use various over-the-counter eyedrops or other medicaments to treat or mitigate diseases of the eye, promote healing, or relieve various irritations. However, many people struggle with using drops due to an involuntary reflex or aversion. Turning away or closing the eye in an instinctual defense against anticipated injury or shaking hands due to anxiety often results in the eye drop landing on the cheek or eyelid which is wasteful of prescription medications and exacerbates the aversion or reflex.

There is a need for methods and apparatus to aid in the accurate placement of ophthalmic solutions into a patient's eye.

SUMMARY OF THE DISCLOSURE

Accordingly, the present invention provides methods and apparatus that support improved ways of administering ophthalmic solutions, including liquid and gel type solutions, of a therapeutic amount, such as a single drop at a time, into an eye of a patient. Eye drops are conveniently dispensed, and consequently more therapeutic, with the apparatus disclosed herein for reliably positioning an eye medicament dispenser in an appropriate position relative to the eye and eye lids and maintain the medicament dispenser at an adequate distance for safety and comfort from the patient's eye. In some embodiments, the present invention provides access to the lower eye lid such that a user may use a free hand to draw down the lower lid to form a recommended 'pocket,' 'pouch,' or 'sack' to receive a common single drop dosage whereby the pocket could hold and distribute the solution over a treated eye.

The present disclosure, in some examples, describes apparatus for securely holding an eye drop dispenser in a fixed position relative to an eye such that the eye drop dispenser may dispense a medicament or other ophthalmic solution in an amount suitable to benefit the patient.

In some examples ophthalmic solutions may be made to be sterile, are packaged, and treated so that they remain sterile. To maintain such sterility, it may be desirable that an uncovered dropper is not touched, and additionally that the dropper is not contacted by any unsterilized surface, such as an eye or face surface of a patient. The present invention maintains the dropper at a distance suitable for dispensing one or more drops of medicament into the patient's eye and prevents the eye dropper from touching the eye or face.

Furthermore, eye droppers may be designed to deliver a single precisely calibrated dosage, which is sufficient to flood the eye without running off. In some examples, it may be desirable that a technique for dispensing eye drops may be to apply a fingertip immediately below the lower eyelid, and with slight pressure, draw the finger down toward the cheek, which will pull the edge of the lower lid down and out to form a crescent pouch. The calibration of the dropper will deliver one drop sufficient to fill the sack which will hold the solution when the eyelid is released, allowing the single dose to be optimally distributed over the surface of the eye.

Moreover, it may be important not to touch the globe of the eye or the cornea with the dropper, as this may contaminate the contents of the dropper or cause damage to the eye itself. Therefore, a safe distance between the dropper and the eye to be maintained when administering the drops is generally desirable. Accordingly, examples are described herein for apparatus and methods that accomplish these desirable characteristics.

One general aspect includes apparatus for administration of an ophthalmic medicament into a patient's eye. The apparatus may include a wearable frame which itself may include: a first receiver, where the first receiver is shaped to engage and align a dispenser that includes the ophthalmic medicament in proximity to the patient's eye; and a frame, where the frame may include structure to support the first receiver and the dispenser, and where the frame may include features to support wearing on a head of the patient. In some examples, the apparatus may function when worn upon the head of the patient and be used to provide support for administration of an ophthalmic medicament. In some examples the apparatus may provide support for the dispenser including the ophthalmic medicament such that the ophthalmic medicament is in a position for dispensing.

Implementations may include one or more of the following features. The apparatus may include guide features, where the guide features facilitate the movement of the dispenser. The movement of the dispenser may include examples where the ophthalmic medicament in the dispenser is moved to be engaged with the receiver. In some examples, the guide features may be v-shaped.

In some examples, the wearable frame may include a wire frame. The wearable frame further may include a nose pad, where the nose pad is formed by a bending of the wearable frame.

The wearable frame may include a plastic body. In some examples, the plastic body may also include a first side piece and a bottom piece which may provide additional support for the frame against the head of the patient. The wearable frame may include a metallic body.

The apparatus may include a second receiver, where the first receiver is positioned to support a treatment above a first eye of the patient while the second receiver is positioned to support a treatment above a second eye of the patient.

In some examples, the guide features and the first receiver may include a continuous molding of the frame around a shaped lens feature, where the shaped lens feature may include a cut out of the lens feature to form a shape of the first receiver and a shape of the guide features. The guide features and the first receiver are formed into a first insert piece, where the first insert piece is engaged to the shaped lens feature. The first insert piece may be a member of a plurality of insert pieces including at least a second insert piece, where the second insert piece, when inserted into the shaped lens feature, locates the dispenser at a different location above the patient's eye when the dispenser is engaged with the second insert piece than the location of the dispenser above the patient's eye when the dispenser is engaged with the first insert piece. The dispenser may include a solution. The dispenser may include a powder.

One general aspect includes a method for administration of ophthalmic medicament in solution into a patient's eye. The method may include placing an apparatus for administration of an ophthalmic medicament into a patient's eye upon a head of the patient. The apparatus for administration of an ophthalmic medicament may include: a wearable frame which in turn may include: a first receiver shaped to engage and align a dispenser including an ophthalmic medicament in proximity to the patient's eye. In some examples, the apparatus may include a frame, suitable to support the first receiver and the dispenser. The frame may include features to support wearing the frame on a head of a patient. In some examples, the apparatus may include guide features, where the guide features facilitate movement of the dispenser including the ophthalmic medicament to be engaged with the receiver.

Methods of the present invention include placing a dispenser containing the ophthalmic medicament into physical interaction with the guide features. The dispenser may be moved into engagement with the first receiver such that engagement with the first receiver supports the dispenser in position for dispensing. The ophthalmic medicament may include dispensing one or more drops of ophthalmic medicament into the patient's eye.

One general aspect includes a method of forming an apparatus for administration of an ophthalmic medicament into a patient's eye. The method may also include molding a plastic material into a shape suitable for bridging a brow, eyes, and nose of a patient. A first shaped piece may be formed with a region excluding plastic material in the shape of a first receiver and a v-shaped set of guide features. In some examples, the user may interact with a dispenser including an ophthalmic medicament with the first v-shaped set of guide features and move the dispenser into engagement with the first receiver. The method may further include using an insert piece shaped to engage with the first shaped lens to guide the dispenser into a suitable position for dispensing the medicament into the patient's eye.

BRIEF DESCRIPTION OF THE DRAWINGS

The accompanying drawings, which are incorporated in and constitute a part of this specification, illustrate several embodiments of the disclosure and, together with the description, serve to explain the principles of the disclosure:

FIG. 10 illustrates method steps that may be taken in some embodiments of the present invention.

FIG. 14 illustrates methods for exemplary embodiments including distance measurements and feedback.

DETAILED DESCRIPTION

The present disclosure provides generally for apparatus and methods for administering an ophthalmic solution into an eye of a patient. In some examples of the invention, a semi-circular receiver may be used to aid initial positioning and optimization of the positioning of an eye dropper in relation to an eye of a user. In some examples, the ophthalmic apparatus may offer an unobstructed field below the dropper through which the upper cheek or lower eyelid may be touched. The ophthalmic apparatus, which may be engaged with an eye dropper, may desirably be positioned reliably. Such positioning may be best accomplished by an apparatus including a bridge, upper frame, temples, and nose pads.

In some examples, the basic elements (such as the bridge, upper frame, temples, and nose pads) may be integrated in a wire form with a horizontal upper frame, temples that rest on or hook over the ears, nose pads, and semi-circular receivers to accept the tip of an eye drop-dispenser bottle. This basic geometry may be enhanced for the purpose of aiding the application of eyedrops by a deep upper horizontal frame that rests on the forehead to prevent the apparatus, and thereby the eye dropper bottle, from approaching the eye too closely. This function may thus, prevent the apparatus from impacting the eye.

Figure 1:
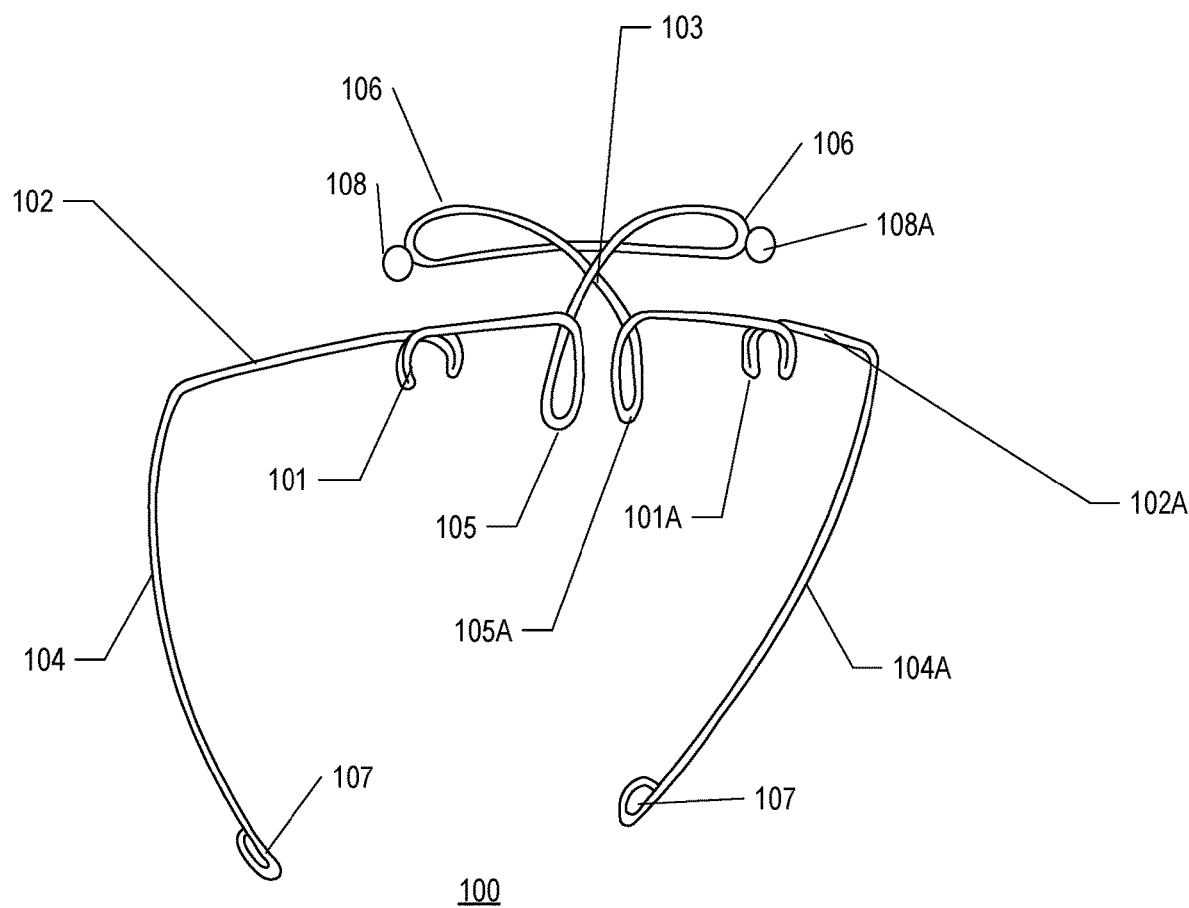
FIG. 1 illustrates exemplary elements of the present invention.

Referring now to FIG. 1, an exemplary apparatus for administration of an ophthalmic medicament 100 of some embodiments of the present invention is illustrated. As illustrated, the apparatus for administration of an ophthalmic medicament 100 may be reusable, although it is possible that some embodiments of the patient are disposable, or preferably, the eye medicament administration apparatus for administration of an ophthalmic medicament 100 may be disposable upon dispensing of a prescribed volume of medicament in a single container of medicament (not shown in FIG. 1, but illustrated as item 302 in FIG. 3).

In some embodiments, a plastic or a wire apparatus for administration of an ophthalmic medicament 100 is shaped to be mounted on a bridge of a nose and supported by the ears of a patient (which may also be referred to herein as a "user"). The apparatus for administration of an ophthalmic medicament 100 may be mounted upon the patient, for example, on one or both of: a bridge of a patient's nose, and over a portion of an ear of the patient, such as over a root of a helix of the human ear. In some examples, a wire is formed into an apparatus for administration of an ophthalmic medicament 100 and mounted on the patient such that it does not significantly interfere with or substantially occlude a field of view of the patient. In this manner, the patient may concentrate for example, upon one or more of: identifying a proper solution bottle, use instructions for a medicament in the solution bottle with an eye dropper for administering a dosage of medicament.

With a cap removed from the bottle of medicament, the patient may position their head back to a preliminary angle. In some examples, with largely unobstructed vision, the patient may bring an eye dropper bottle close to the ophthalmic apparatus until the neck of the eye dropper engages a dropper receiver 101 for securing the eye dropper in a position above the eye of the patient. In some preferred embodiments (as illustrated in FIG. 1), the dropper receiver 101 may include a semi-circular wire formation sized to provide a compressive force around a neck of the medicament bottle that secures the medicament bottle in place while the medicament is administered into the eye of the patient and the bottle is supported by the apparatus for administration of an ophthalmic medicament 100.

With the bottle of medicament engaged by the apparatus for administration of an ophthalmic medicament 100, the user may tilt their head back and look up as a patient would naturally do in such circumstances.

Preferably, the apparatus for administration of an ophthalmic medicament 100 is designed such that the eyedropper may be positioned slightly above the user's normal horizontal line of sight to relieve a typically perceived necessity of tilting the head to an extreme and uncomfortable position. Such an improved position may prevent strain for those with orthopedic or muscular limitations of the neck. With the eye dropper thus aligned over the eye, the patient or another person may engage the tip of a finger of a hand to draw down a lower lid of a patient to form a recommended pouch to receive one or more drops of the administered medicament. The user may squeeze the eye dropper bottle to dispense the drop with confidence in safety and efficiency and repeat the process for the other eye as desired or prescribed.

Basic elements of some examples of the present invention may include a dropper receiver 101 that may be semi-circular in shape, or another shape that is conducive to supporting the eye dropper, to aid initial and optimum positioning of the eye dropper in relation to the eye. The apparatus for administration of an ophthalmic medicament 100 may provide an unobstructed field below the dropper through which the upper cheek or lower eyelid may be touched. The dropper receiver 101 reliably supports the eye dropper in a position conducive to administering drops of an eye medication from the dropper into the eye. In some preferred embodiments, the apparatus for administration of an ophthalmic medicament 100 may include an upper half of an upper frame 102. The apparatus for administration of an ophthalmic medicament 100 may also include a bridge 103, upper frame 102, temples 104, nose pads 105, and earpieces 107 for fitting behind the ears to a patient.

These bridge 103, frame 102, temples 104, and nose pads 105 may be integrated in a wire form with a horizontal upper frame 102, temples 104 that rest on or hook over the ears of a patient, nose pads 105, and semi-circular dropper receivers 101 to accept an eye drop-dispenser bottle. In some embodiments, a focal artifact 108-108A may be positioned within the apparatus for administration of an ophthalmic medicament 100 in a location such that when the apparatus for administration of an ophthalmic medicament 100 is mounted on the face of a patient, a focal artifact 108-108A is above an eye of the patient in a position that is conducive to the patient opening their eye wide enough to receive a drop of the medicament when the drop of medicament is deposited from an eye dropper secured in the dropper receiver 104. For example, as illustrated an apparatus for administration of an ophthalmic medicament 100 may include a right focal element 108 and a left focal element 108A. The right focal element 108 may be positioned above the right eye of the patient while the right upper frame 102 and the left upper frame 102A are positioned over the brow of the patient. Similarly, the left focal element 108A may be positioned above the left eye of the patient while the right upper frame 102 and the left upper frame 102A are positioned over the brow of a patient.

The illustrated geometry of a wire formed into the bridge 103, frame 102, temples 104, and nose pads 105 may be enhanced for the purposes of aiding the application of eyedrops by a formable frame expansion 106 that may be positioned to rest on a forehead of a patient and support the eye dropper is a position that prevents the apparatus for administration of an ophthalmic medicament 100 and the eye dropper bottle from approaching the eye too closely and preventing injury to the patient's eye.

In some embodiments, an apparatus for administration of an ophthalmic medicament 100 into a patient's eye may include a right upper frame 102, and a left upper frame 102A, the right upper frame 102 and the left upper frame 102A may be connected via a bridge 103, which may include a formable frame expansion 106 extending upward from the right upper frame 102 and the left upper frame 102A sufficiently to contact a forehead of the patient while the right upper frame 102 and the left upper frame 102A are positioned over a brow of the patient. Contact of the formable frame expansion 106 to the forehead is useful for providing upper support of the right upper frame 102 and the left upper frame 102A and setting and maintaining the dropper receiver(s) 101-101A at a correct distance from a patient's eye for administering a drop of medicament from a dispenser and also maintain a correct distance from the patient's eye to prevent contact of the dispenser and the eye.

As illustrated in FIG. 1, in some embodiments, a right nose pad 105 and a left nose pad 105A may be sized and positioned to rest upon a right nose side and a left nose side respectively of the patient. The right nose pad 105 and a left nose pad 105A provide lower support of the right upper frame 102 and the left upper frame 102A while the right upper frame 102 and the left upper frame 102A are positioned over the brow of the patient. Such support provided by the right nose pad 105 and the left nose pad 105A will also set and maintain the dropper receiver(s) 101-101A at a correct distance from a patient's eye for administering a drop of medicament from a dispenser and also maintain a correct distance from the patient's eye to prevent contact of the dispenser and the eye.

A right temple 104 is extendable from the right upper frame 102 over a right ear of the patient when right upper frame 102 is positioned over the brow of the patient; and a left temple 104A is extendable from the left upper frame 102A over a left ear of the patient when left upper frame 102A is positioned over the brow of the patient.

The right upper frame 102 and the left upper frame 102A support a first dropper receiver 101. The dropper receiver 101 is shaped to engage and align a dispenser containing an ophthalmic medicament in a position suitable for dispensing a drop of the ophthalmic medicament into the patient's eye. The dropper receiver 101 is also capable of engaging the dispenser to prevent the dispenser from contacting the patient's eye while the right upper frame 102 and the left upper frame 102A are positioned over the brow of the patient and the right nose pad 105 and the left nose pad 105A rest upon the right nose side and the left nose side of the patient respectively.

In some embodiments, the apparatus for administration of an ophthalmic medicament 100 into a patient's eye is formed from a contiguous item of wire which may be formed or otherwise shaped vias mechanical manipulation to provide a desired shape.

Additionally, some embodiments may have one or both right nose pad 105 and the left nose pad 105A formable, such as via bending the wire used to form or support the right nose pad 105 and the left nose pad 105A to adjust one or more of: contact with the patient's nose, distance from an engaged receiver to the eye of the patient, position of the dropper receiver 101 over the patient's eye; or other variable.

Embodiments may also include multiple dropper receivers, such as a right dropper receiver 101 constituting a first dropper receiver and a left dropper receiver 101A constituting a second dropper receiver. Additional dropper receivers are within the scope of the invention. By way of non-limiting example the right dropper receiver 101 may be positioned to support a dispenser above a right eye of the patient to provide a treatment including administration of a medicament to the right eye, while the left dropper receiver 101A is positioned to support a treatment including administration of a medicament to the left eye of the patient.

Preferred embodiments include a dispenser that contains and administers a solution and/or a suspension including an ophthalmic medicament.

In some embodiments, after a seal and cap or other packaging is removed from an eye dropper bottle, a patient may tip their head back to a preliminary angle in an instinctive action. Again, with largely unobstructed vision, the patient may position the eye dropper bottle in the apparatus until the neck of the dropper engages the semi-circular receivers 101 of the apparatus for administration of an ophthalmic medicament 100. With the dropper bottle engaged by the apparatus for administration of an ophthalmic medicament 100, the patient may tilt their head farther back and look upwards as may occur naturally.

The apparatus for administration of an ophthalmic medicament 100 may be designed such that the eyedropper is positioned slightly above the user's normal horizontal line of sight to relieve the typically perceived necessity of tilting the head to an extreme and uncomfortable position. The apparatus for administration of an ophthalmic medicament 100 may therefore, prevent strain for those with orthopedic or muscular limitations of the neck. With the eye dropper thus aligned over the eye, the patient may use the tip of a finger of the unoccupied hand to draw down their lower lid to form the recommended pouch to receive the drop. The patient may then squeeze the eye dropper bottle to dispense the drop with confidence in safety and efficiency and repeat the process for the other eye as desired or prescribed.

Figure 2:
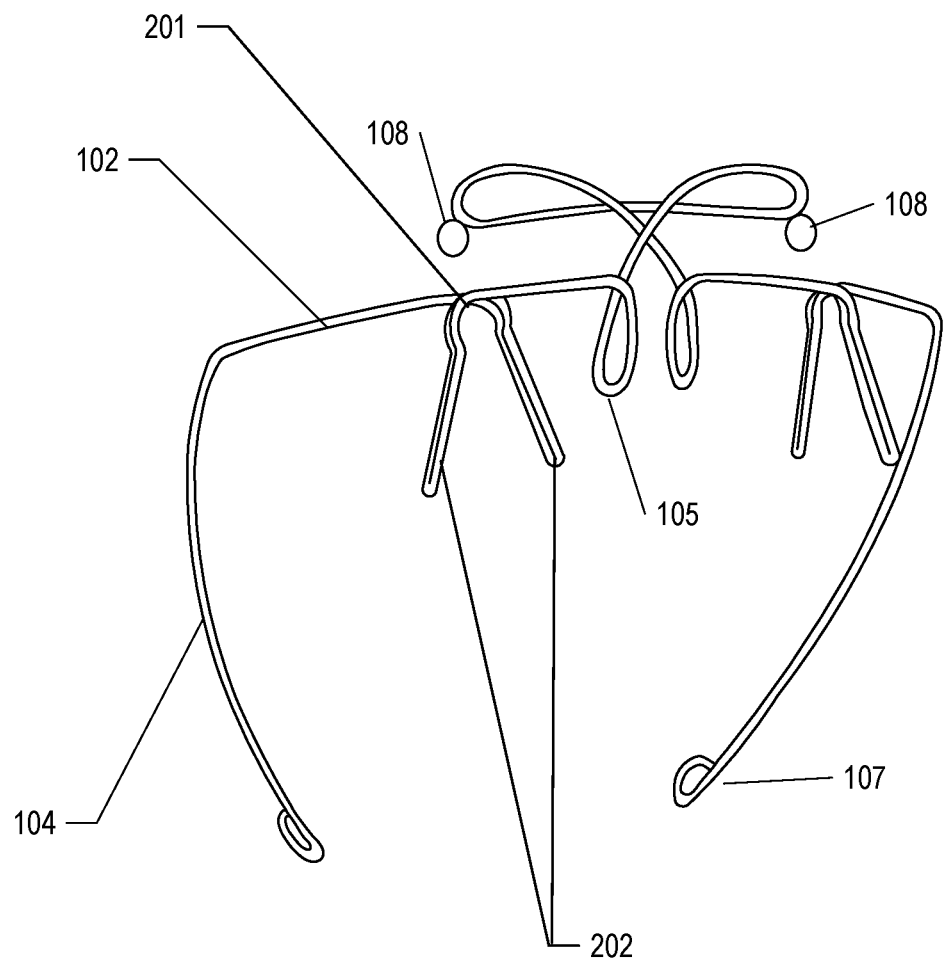
FIG. 2 illustrates an exemplary embodiment with V shaped guides.

Referring now to FIG. 2, an illustration of an enhancement of the basic embodiment that includes V-shaped guides 202 integrated with the semi-circular receivers 201 is presented. The V-shaped guides 202 allow the flanks of an eye dropper's tip to be engaged with the apparatus while requiring less accuracy than that needed to engage the smaller semi-circular receiver. Once the eye dropper engages with the V-shaped guide, the eye dropper may be moved along it until seated in the semi-circular receiver.

Figure 3:
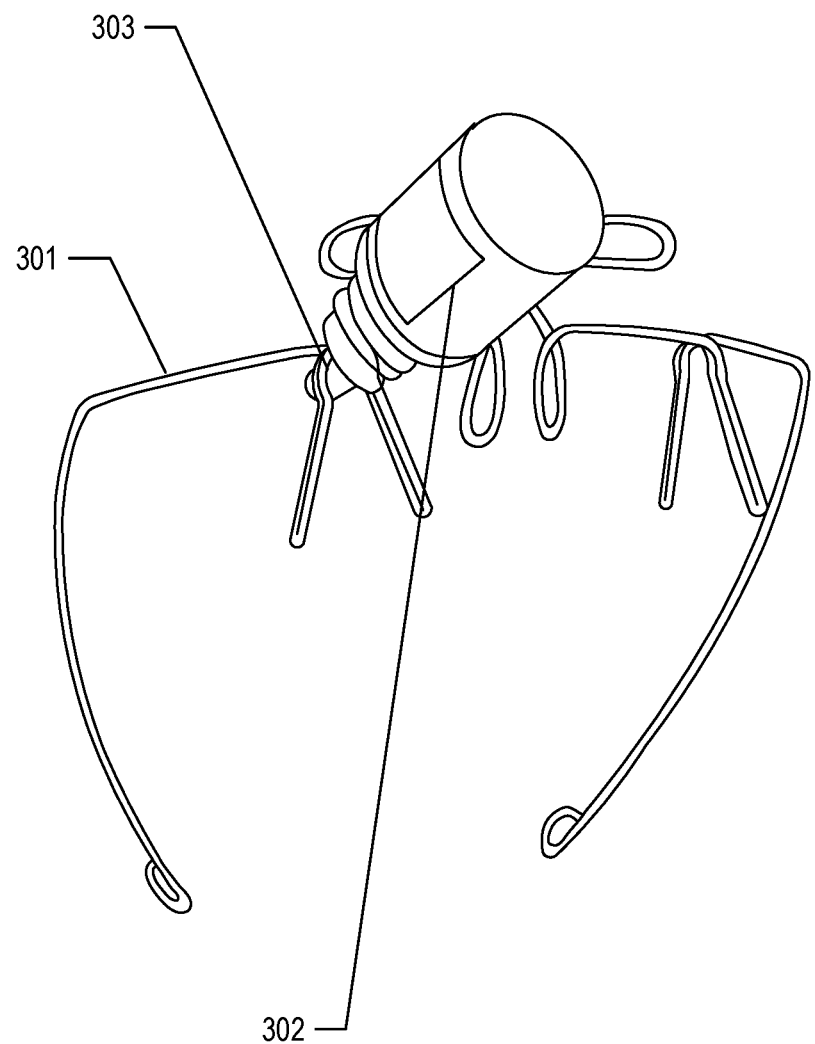
FIG. 3 illustrates an exemplary apparatus for administration of an ophthalmic medicament.

FIG. 3 illustrates an eye-dropper bottle 302 engaged in an enhanced receiver 303 that guides the bottle into position in the enhanced apparatus 301. This enhanced apparatus 301 may be used to assist individuals with neuromuscular deficiencies affecting fine motor control, and allow a person otherwise incapable of self-administration of medicaments to be able to accurately place drops of a medicament into the patient's own eye.

Figure 4:
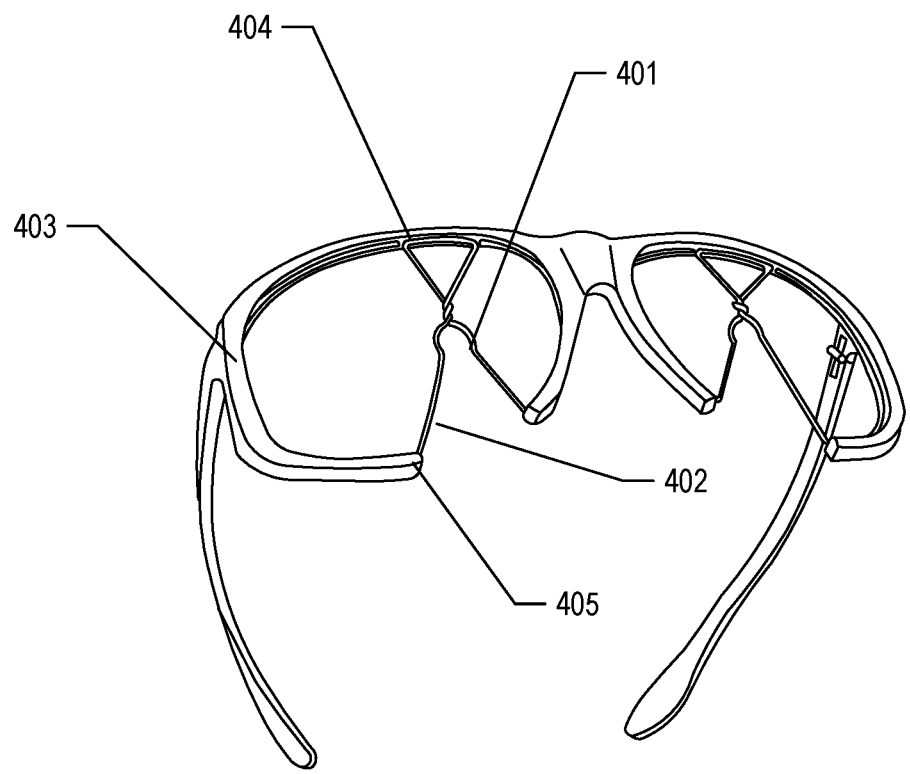
FIG. 4 illustrates exemplary semi-circle receivers in a plastic form.

Referring now to FIG. 4, in some additional embodiments of the present invention, a modification of the design of common eye glass frames 403 includes portions of the frame 404, 405 that ordinarily hold the lenses incorporates the V-shaped guides 402 and semicircular receivers 401 as shown in FIG. 4. This embodiment may inspire greater confidence for the user in that it resembles traditional eyewear in form and fit.

Figure 5:
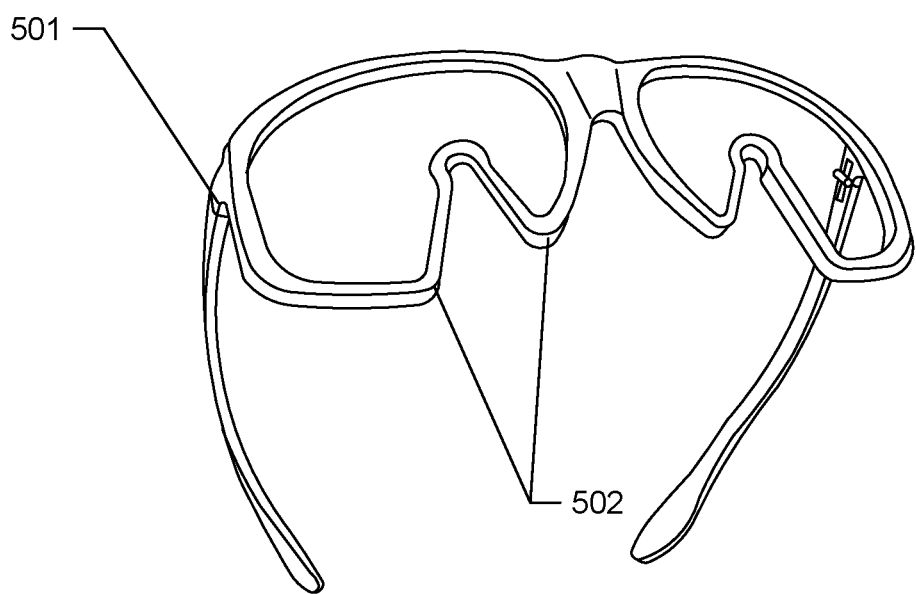
FIG. 5 illustrates exemplary embodiments with a lower arc cut away.

A similar embodiment shown in FIG. 5 may be based on common eye glass frames 501 from which a section 502 of the lower arc may be cut away. Other means to form such an apparatus may be employed. The V-shaped guides 502 are then manufactured from wire forms that may be inserted into the frame, secured by heating, and pinching the frame (in the case of thermoplastic materials), adhesives, or by an interference fit facilitated by the spring-like characteristics of certain types of wire.

Figure 6:
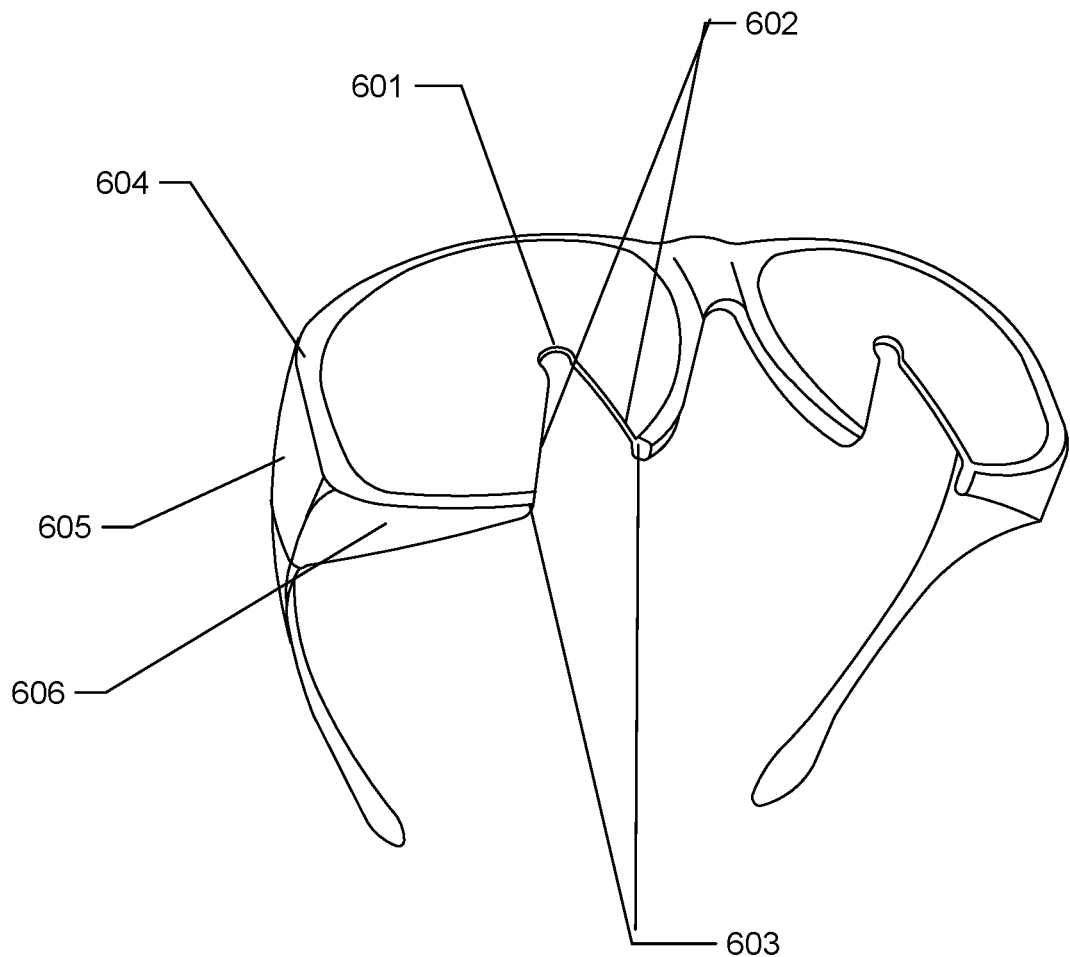
FIG. 6 illustrates an exemplary semi-circle cut away.

Proceeding to the illustration in FIG. 6, a fourth exemplary embodiment is a form which may result from a modification of a common design of protective eyewear 604 provided to patients of recent eye surgery or with hypersensitivity to light. These wrap-around frames with panels on the first side piece 605 and bottom piece 606 may be designed to be positioned upon a patient in a manner similar to fitting the patient with eyeglasses, and as such, fit the face with space between the eye and the plane of a plastic surface replacing a typical lens portion of a pair of eyeglasses. Such wrap-around frames may be manufactured with integral plastic surfaces, the modification of which consists of removing a section 603 of the lower frame and integral lens to create the V-shaped guide 602 and semi-circular receiver 601.

The frame and plastic surface may be of various dimensions to suit variations in the width of the users' temples, proportions of the bridge of the nose, or of smaller proportions suitable for school-aged children. The lenses may be clear to avoid claustrophobia and permit an unobstructed view of the environment and eye dropper to remove or replace the cap, and for the initial action to position the dropper. Tinting the plastic surface may provide a benefit of deemphasizing the surroundings to aid concentration on the matter at hand and blocking light with which the patient may see a drop approaching their eye so that the patient's blink reflex is subdued or eliminated until the drop is in contact with the eye and/or in a pouch formed by a lower eyelid.

The frame, wire form and lens material of each of these embodiments must be selected to permit frequent disinfection by application of a suitable solution. The modification or manufacture of the wire forms or lenses may be made in a manner that does not create surface textures, porosity or scratches that may harbor harmful bacteria or viruses and possibly shield them from sterilization methods.

Figure 7:
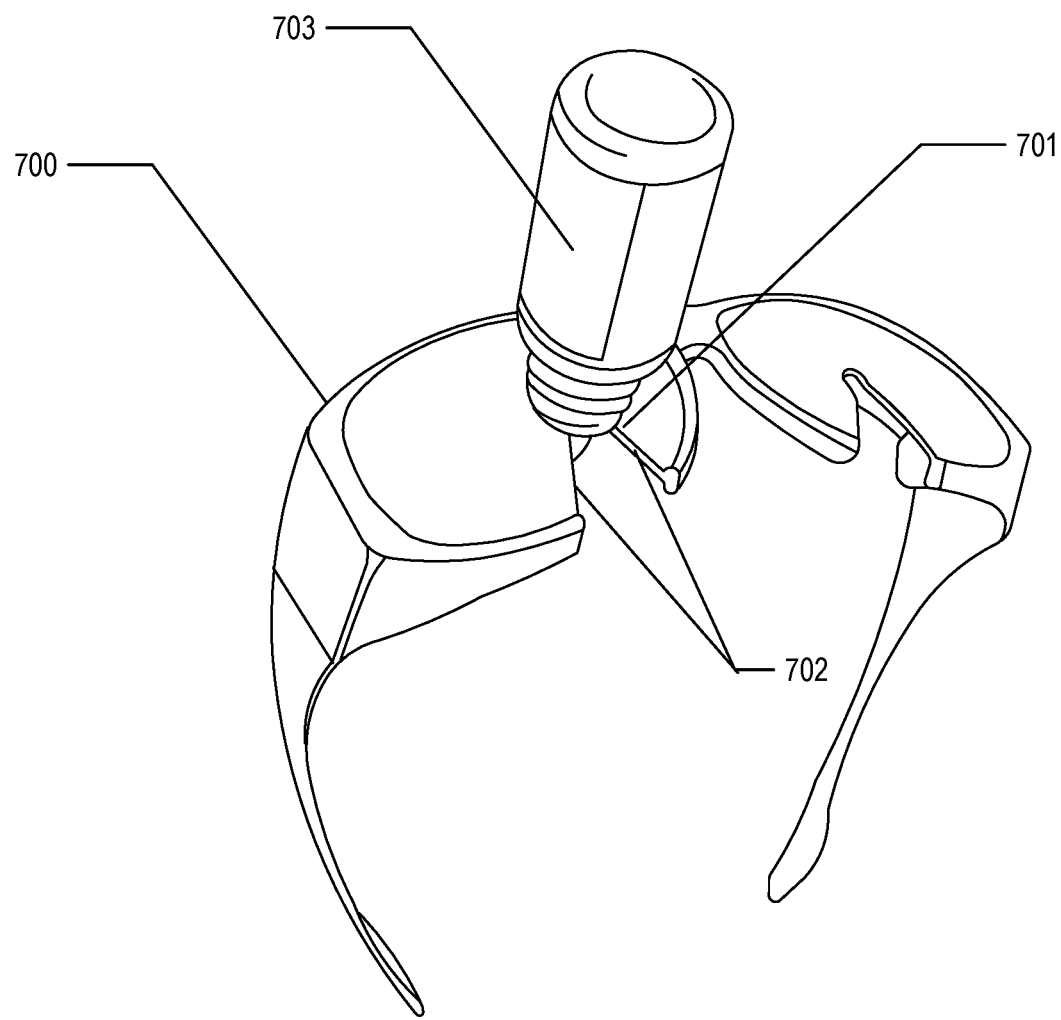
FIG. 7 illustrates exemplary embodiments with dispenser positioned in an ophthalmic solution dispensing device.

FIG. 7 illustrates how the eye dropper bottle or other dispenser 703 may be positioned in the circular feature 701 formed into the plastic surface, and a guide 702 in the eyewear 700. The sides of the guide 702 may divaricate from the circular feature 701 to provide a narrowing V-shaped guide to facilitate bringing the dispenser 703 into position.

Figure 8:
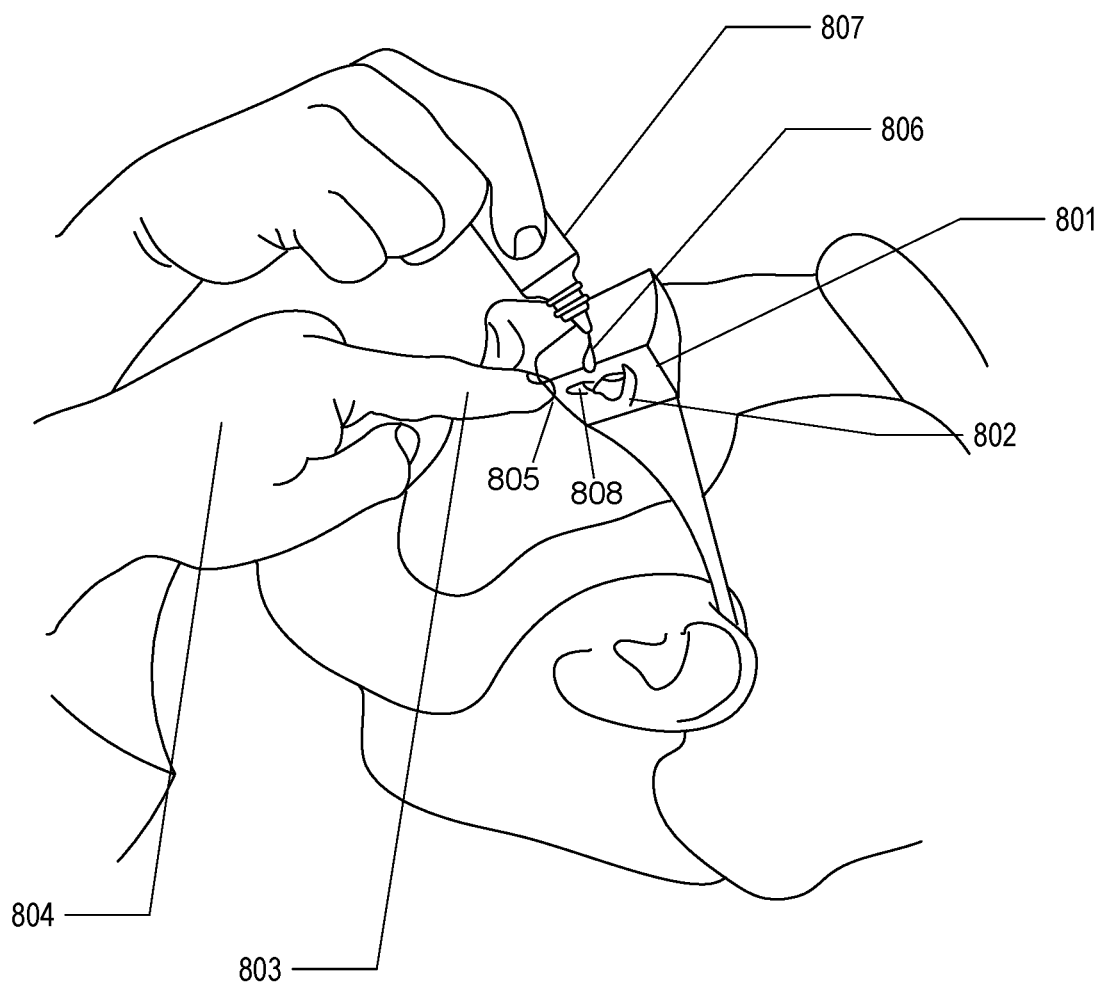
FIG. 8 illustrates additional exemplary apparatus for administration of an ophthalmic medicament positioned on a patient.
Figure 8A:
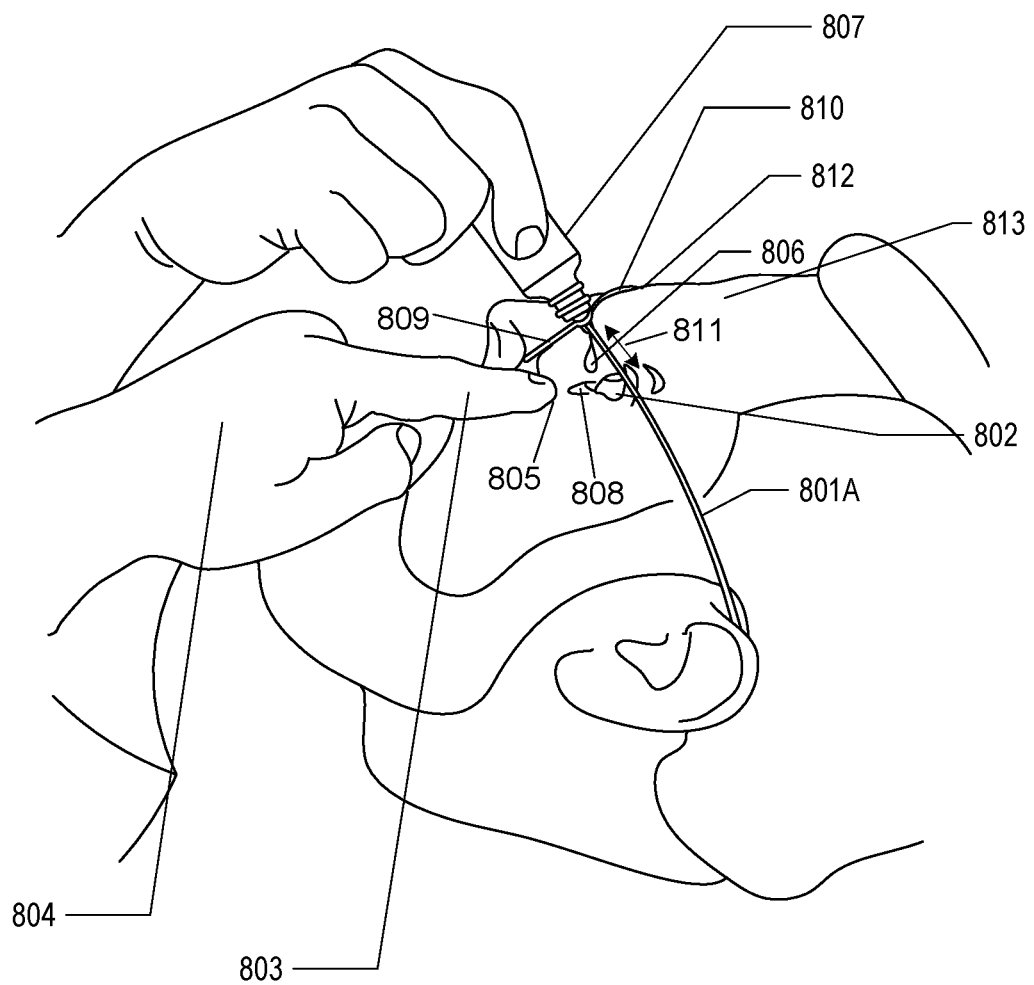
FIG. 8A illustrates exemplary wire formed apparatus for administration of an ophthalmic medicament positioned on a patient.

Referring now to FIG. 8a schematic diagram illustrates how an apparatus for administration of an ophthalmic medicament 801 into a patient's eye, positions a dispenser 807 above an eye 802 of a patient. In some embodiments, a finger 803 of a hand 804 may draw down a lower lid 805 of the patient to create a crescent sack 808 into which a drop 806 of medicament may be accurately deposited.

It may be observed that individuals have different facial features and proportions such that the position of an eye dropper or other dispenser 807 in one version of the apparatus may be suboptimal for another portion of the population.

Referring now to FIG. 8A, in some embodiments, and in some methods of use, differences caused by facial proportions may be mitigated to a degree by forming a wire 809 used to fashion the apparatus for administration of an ophthalmic medicament 801A. For example, in some embodiments, a formable frame expansion 106 may be formed (such as via bending the wire) to adjust a distance 811 of the dispenser 807 from a patient's eye 802 while the formable frame expansion 810 rests on the patient's brow 812 or forehead 813.

In some methods of administering a drop 806 of ophthalmic medicament, an angle of a patient's head while dispensing the eye drop may be changed. But these accommodations may not be adequate, comfortable, or achievable. In some examples, the result may be further enhanced by providing interchangeable receivers that fit at the apex of the V-shaped guides. Such interchangeable receivers might be available in pairs of various dimensions that may be selected to optimize the position of the eyedropper in relation to the eye and the pouch of the distended lower eye lid.

Figure 9:
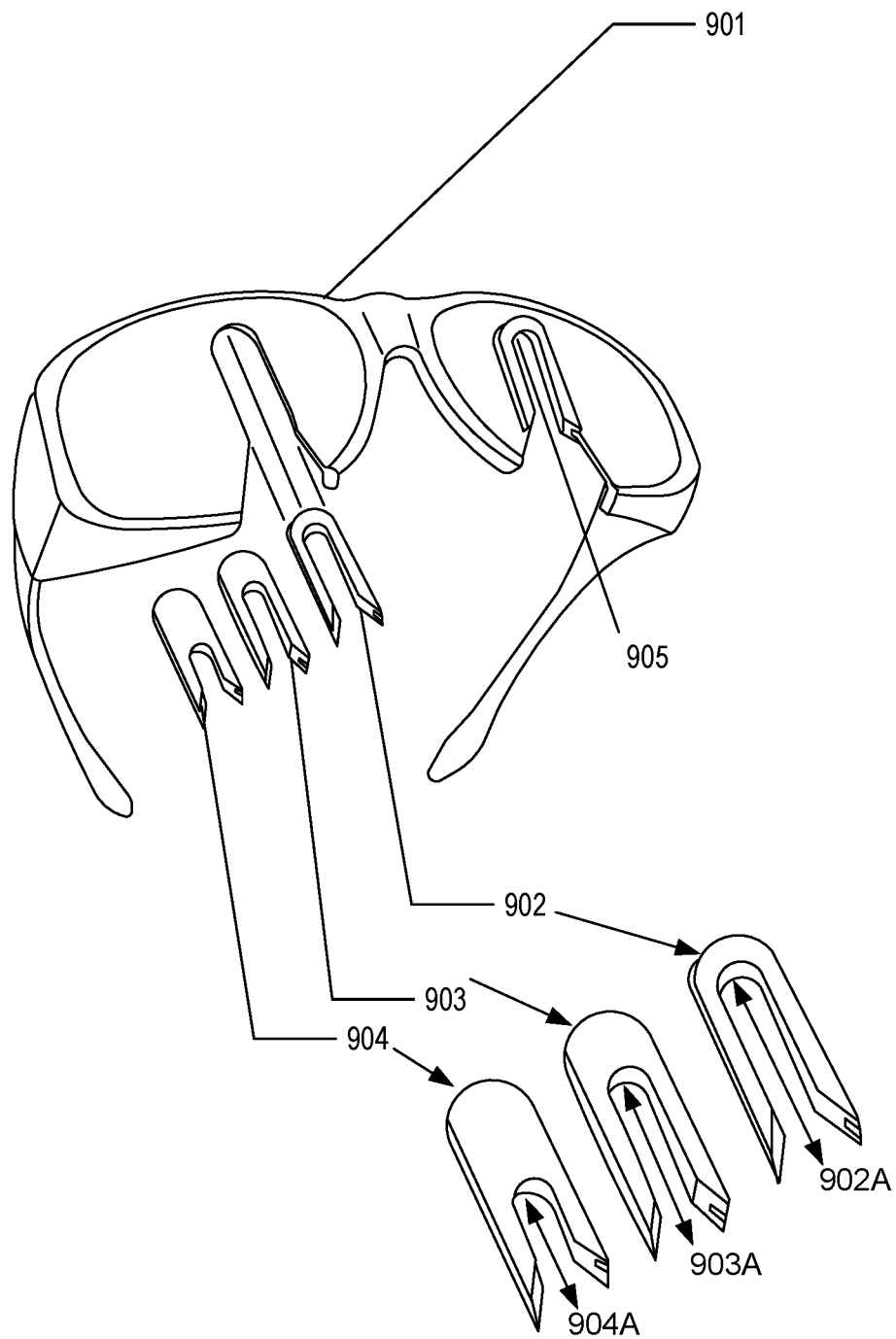
FIG. 9 illustrates additional exemplary embodiments with inserts of assorted sizes to receive an ophthalmic solution dispenser.

Referring now to FIG. 9, an exemplary embodiment with inserts 902-905 of assorted sizes to receive an ophthalmic solution dispenser are illustrated. According to such embodiments, an insert may be mounted in a plastic form 901 type ophthalmic solution dispenser frame. The plastic form may be of a size and shape suitable to bridge a patient's brow, eye, and nose, and support a dispenser in a position and at a height conducive to safe administration of medicament from the dispenser into the patient's eye. In various embodiments, an insert may be sized to receive a particular ophthalmic solution dispenser which may have a particular size and shape. Other embodiments may include one or more standardized sizes and shapes of dispensers and corresponding shaped inserts 902-905.

As illustrated in the blow ups of inserts 902-904, different inserts 902-904 may have positioning slots 902A-904A that allow for a user to adjust for placement of the dispenser above the patient's eye. Adjustment is accomplished by choosing an insert 902-904 with a correct corresponding length positioning slot 902A-904A.

FIG. 10 is a flowchart of an example process 1000. In some implementations, one or more process blocks of FIG. 1 may be performed by a device.

As illustrated, process 1000 may include placing an apparatus for administration of an ophthalmic medicament into a patient's eye upon a head of the patient, where the apparatus for administration of an ophthalmic medicament may include: a wearable frame having: a first receiver, where the first receiver is shaped to engage and align a dispenser having the ophthalmic medicament in proximity to the patient's eye; a frame, where the frame may include structure to support the first receiver and the dispenser, and where the frame may include features to support wearing on a head of the patient; guide features, where the guide features facilitate to movement of the dispenser having the ophthalmic medicament to be engaged with the receiver (block 1002).

For example, device may place an apparatus for administration of an ophthalmic medicament into a patient's eye upon a head of the patient, where the apparatus for administration of an ophthalmic medicament may include: a wearable frame having: a first receiver, where the first receiver is shaped to engage and align a dispenser having the ophthalmic medicament in proximity to the patient's eye; a frame, where the frame may include structure to support the first receiver and the dispenser, and where the frame may include features to support wearing on a head of the patient; guide features, where the guide features facilitate to movement of the dispenser having the ophthalmic medicament to be engaged with the receiver, as described above.

Process 1000 may include where when worn upon the head of the patient the apparatus for administration of an ophthalmic medicament supports the dispenser having the ophthalmic medicament such that the ophthalmic medicament is in a position for dispensing (block 1004). For example, device may where when worn upon the head of the patient the apparatus for administration of an ophthalmic medicament supports the dispenser may include the ophthalmic medicament such that the ophthalmic medicament is in a position for dispensing, as described above.

As further shown in FIG. 10, process 1000 may include placing the dispenser having the ophthalmic medicament into physical interaction with the guide features, where the guide features direct further movement of the dispenser towards the first receiver (block 1006). For example, device may place the dispenser having the ophthalmic medicament into physical interaction with the guide features, where the guide features direct further movement of the dispenser towards the first receiver, as described above.

As also shown in FIG. 10, process 1000 may include moving the dispenser into engagement with the first receiver, where with engagement with the first receiver the dispenser having the ophthalmic medicament is supported in position for dispensing (block 1008). For example, device may move the dispenser into engagement with the first receiver, where with engagement with the first receiver the dispenser having the ophthalmic medicament is supported in position for dispensing, as described above.

At block 1012, the frame may be formed with wire; and at block 1014, a frame and a lens shaped piece may be formed with plastic to support the medicament container.

Figure 11:
FIG. 11 illustrates additional method steps that may be taken in some embodiments of the present invention.

Referring now to FIG. 11, in some embodiments, at block 1101, a plastic material (and/or a wire) may be molded into a shape suitable for bridging a brow, eye(s), and nose of a patient. At block 1102 an insert piece may be used to locate a dispenser in a position suitable for dispensing ophthalmic medicament into a patient's eye.

In the preceding sections, detailed descriptions of examples and methods of the disclosure have been described. The description of both preferred and alternative examples though thorough are exemplary only, and it is understood that to those skilled in the art that variations, modifications, and alterations may be apparent. It is therefore to be understood that the examples do not limit the broadness of the aspects of the underlying disclosure as defined by the claims.

Distance Tracking and Feedback

Figure 12:
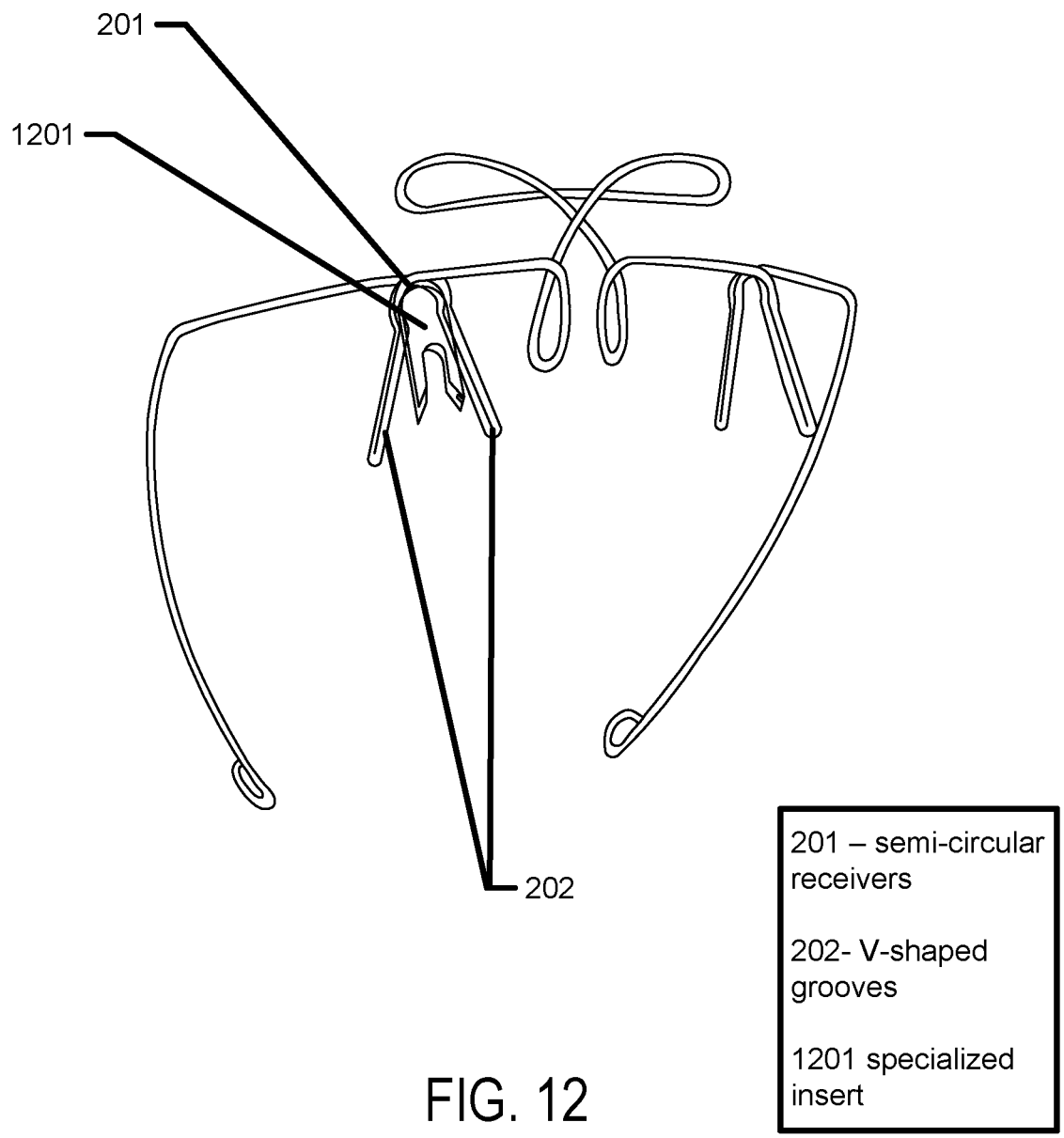
FIG. 12 illustrates additional exemplary embodiments including distance measurements and feedback and inserts.

Referring now to FIG. 12 an illustration of an exemplary embodiment with a wire form supporting structure comprising V shaped grooves 202 and semi-circular receivers 201 in concert with a specialized insert 1201 that may insert into the semi-circular receivers 201. In some examples, the specialized insert 1201 may include components to measure a distance from a surface of the specialized insert 1201 to a surface of a user's eye. Furthermore, it may include feedback means to the user. In addition, the specialized insert 1201 may include the functions as described previously relative to inserts of engaging a medicament container and holding it in a place. The wire form supporting structure or other supporting structures with flexibility may all the use to flex the structure by applying force upon a medicament container interfaced with the insert and supporting structure. Although examples of distance measurement and feedback capabilities are illustrated here and in following steps in embodiment examples of an insert, in other embodiments the various functions and apparatus may be incorporated in other ways such as being integrated as a part of the supporting structure as a non-limiting example.

Figure 13:
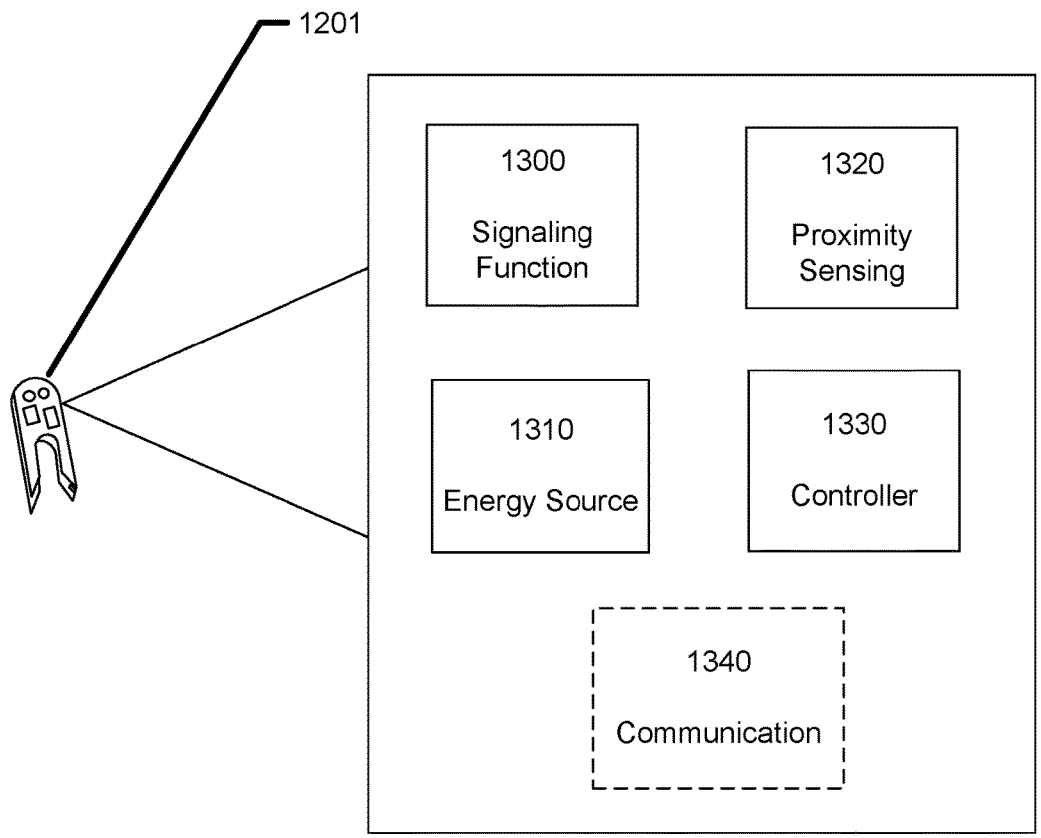
FIG. 13 illustrates functional blocks of exemplary embodiments including distance measurements and feedback.

Referring now to FIG. 13, an illustration of exemplary functional elements for distance tracking and feedback is provided. In some examples, one or more of these elements may be incorporated into a structure, and various combinations may be possible. Overall, one example of a purpose of the functional elements is to allow a user to position a medicament container interface with any of the various examples of supporting structures and associated componentry in proximity to a user's eye. Thereafter, a distance determination between a part of an insert or the supporting structure itself may be made and compared to a desired range of distances for the dispensing of the treatment. There may be numerous of the functional elements illustrated in FIG. 13 to perform this function.

A signaling function 1300 may be incorporated into a specialized insert 1201 in some examples. The signaling function may include light generating components. In an example, two small LED devices may be included such as one green LED and one red LED. The activation of a green LED may be visible to the user and indicate that an appropriate distance for dispensing has been established. There may be other signaling means in addition to light generating devices or instead of them such as haptic or vibrational elements that would shake the structure lightly which may be felt by a hand of a user positioning the medicament container. In such an example, the user may position the medicament container into the insert and thereafter flex the structure towards the user's eye surface. The signaling function 1300 may be activated when the distance enters a range of acceptable values, and a shaking may be initiated in some examples.

The activation of a signaling function may require an energy source 1310 to provide it the energy for a light generating source, a haptic or vibrational source of for other signaling means. Accordingly, the energy source 1310 may be included within the apparatus. In some examples, the energy source may include a battery element. In other examples, the energy source may include energy harvesting components such as solar cells, RF coils, thermoelectric devices and the like that may receive energy from the environment. In some examples, a wireless transmission of energy may be engaged and received by an energy source 1310.

In some examples, a proximity sensing 1320 function may be incorporated into the apparatus to measure the distance from a reference point on the insert or holding structure to a surface of a user's eye. In some examples, the distance would be measured to the perpendicular of the surface that the proximity sensing 1320 function is affixed to, in other examples more complicated sensing may involve multiple paths of distance assessment. In some examples, a sensing capability of the proximity sensing 1320 function may involve use of an ultrasonic source of sound or other types of sound sources. The sound would be emitted at the sensing element proceed through the air between the sensing element and a user's eye and reflect back. The time for the round trip could be used and based on the speed of sound in the air medium a distance may be calculated. In some such examples, an element within the proximity sensing 1320 function may also measure a temperature of the ambient for higher precision. In another type of sensing example, light may be reflected off the eye surface and detected at a sensor. Although time of flight may be used in some examples, in other examples, the light source may be angled at a known angle and the sensor positioned in such a manner that reflected light would be maximally received at the sensor when the surface of the eye is at a particular distance from the source of light. The various means of determining the distance may include sophistication to detect blinking of a user. Although the user may be able to perform the dispensing of medicament while stopping their blinking, in other examples it may be desirable to detect the action of a blink and await the period when the eye is open. In some examples, rudimentary camera type detectors may be employed both to assess a blink state and also to support distance measurements based on typical sizing of features such as user's iris diameter.

In some examples, a controller 1330 may be incorporated within the apparatus. The controller may be capable of assessing a status of the energy source 1310 and interacting with the proximity sensing 1320 function as well as controlling the signaling function 1300. In some additional examples, a communication means 1340 may also be included within the apparatus or within the controller 1330. The communication means may allow for the coordination of the distance sensing function of the apparatus with outside devices. In some examples, a smart device may be able to pair with the communication function and may provide signaling means, such as by the production of a sound on the smart device. In some other examples, the medicament container may include a capability of dispensing a medicament when it receives a communication signal. Accordingly, when the controller 1330 determines that a distance of separation has been reached by the user pressing the medicament storage towards or away from their eye, a signal may be processed through the communication means 1340 and received at the medicament storage device to automatically dispense the medicament. In other examples, the signal, such as a green led light, may allow the user to activate dispensing of the medicament by physical means.

Referring now to FIG. 14, a method of utilizing a distance sensing function and signaling means is illustrated. At block 1410, the method may include a step to obtain a medicament dispensing support structure with a distance sensing means. The method may continue at block 1420, with a step to interface a medicament storage element with the dispensing support structure. The method may further continue at block 1430 with a step to position the medicament dispensing support structure and the distance sensing means upon the head of the user. At block 1440, an optional step may include initializing the distance sensing means. In some examples a button may be located upon the apparatus for initializing. In some examples, a wireless signal may be used to initialize. In some examples, movement of the apparatus may be sensed and initialize the distance sensing means. Continuing at block 1450, the method may include a step to flex the frame of the medicament dispensing support structure to move the distance sensing means towards or away from the user's eye surface. The method may further include a step at block 1460 for the apparatus to signal or electronically communicate from the apparatus when a distance within a desired range is sensed. In some cases, the method may also include a step at block 1470 to dispense the medicament.

CONCLUSION

A number of embodiments of the present disclosure have been described. While this specification contains many specific implementation details, they should not be construed as limitations on the scope of any disclosures or of what may be claimed, but rather as descriptions of features specific to particular embodiments of the present disclosure. While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the form disclosed, but to the contrary, the present disclosure is to cover all modification, equivalents and alternatives falling within the spirit and scope of embodiments of the present disclosure as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

The phrases "at least one," "one or more," and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising," "including," and "having" can be used interchangeably.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while method steps may be depicted in the drawings in a particular order, this should not be understood as requiring that such operations be performed in the particular order shown or in a sequential order, or that all illustrated operations be performed, to achieve desirable results.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. Apparatus for administration of an ophthalmic medicament into a patient's eye, the apparatus comprising:
   a right upper frame and a left upper frame, the right upper frame and the left upper frame connected via a bridge comprising a formable frame expansion extending upward from the right upper frame and the left upper frame and through the bridge to sufficiently to contact a forehead of a patient located above a brow of the patient while the right upper frame and the left upper frame are positioned over the brow of the patient, and to provide upper support of the right upper frame and the left upper frame;
   a formable right nose pad and a formable left nose pad, sized to rest upon a right nose side and a left nose side respectively of the patient to provide lower support of the right upper frame and the left upper frame while the right upper frame and the left upper frame are positioned over the brow of the patient;
   a right temple extendable from the right upper frame over a right ear of the patient when the right upper frame is positioned over the brow of the patient;
   a left temple extendable from the left upper frame over a left ear of the patient when the left upper frame is positioned over the brow of the patient;
   the right upper frame and the left upper frame supporting a first dropper receiver shaped to engage and align a dispenser containing the ophthalmic medicament in a position suitable for dispensing a drop of the ophthalmic medicament into the patient's eye and prevent the dispenser from contacting the patient's eye while the right upper frame and the left upper frame are positioned over the brow of the patient and the formable right nose pad and the formable left nose pad rest upon the right nose side and the left nose side of the patient respectively; and
   the right upper frame and the left upper frame supporting a distance measuring means and a signaling means, wherein the distance measuring means is functional to assess a distance of the first dropper receiver from a surface of the patient's eye;
   wherein,
   the apparatus for administration of the ophthalmic medicament into the patient's eye is formed from a contiguous item of wire;
   the formable frame expansion further includes a left portion and a right portion; and
   the contiguous item of wire extends from the formable right nose pad and through the bridge to form the left portion of the formable frame expansion, and further extends to form the right portion of the formable frame expansion opposite the left portion of the formable frame expansion, cross the bridge, and form the formable left nose pad.

2. The apparatus of claim 1, further comprising:
guide features fixedly attached to the first dropper receiver and extending outward from the first dropper receiver at an angle conducive to facilitate movement of the dispenser containing the ophthalmic medicament into engagement with the first dropper receiver;
a left focal element formed on the left portion of the formable frame expansion; and
a right focal element formed on the right portion of the formable frame expansion.

3. The apparatus of claim 2 wherein the guide features are positioned in a V-shape with a wide opening tapering to a more narrow connection to the first dropper receiver.

4. The apparatus of claim 3 wherein the formable right nose pad and the formable left nose pad are formable by a bending a wire to adjust contact with a patient's nose.

5. The apparatus of claim 1, wherein the right upper frame and the left upper frame comprise a plastic body.

6. The apparatus of claim 5, further comprising at least a first side piece and a bottom piece, wherein the first side piece and the bottom piece provide additional support for a frame against a head of the patient.

7. The apparatus of claim 1, wherein the right upper frame and the left upper frame comprise a metallic body.

8. The apparatus of claim 1, further comprising a second dropper receiver, wherein the first dropper receiver is positioned to support the dispenser above a right eye of the patient while the second dropper receiver is positioned to support a treatment above a left eye of the patient.

9. The apparatus of claim 1, wherein the apparatus for administration of the ophthalmic medicament into the patient's eye is formed from a single item of plastic.

10. The apparatus of claim 9, comprising a continuous molding of a frame around a plastic surface comprising the first dropper receiver.

11. The apparatus of claim 10, wherein the plastic surface comprises guide features positioned adjacent to the first dropper receiver and extending outward from the first dropper receiver at an angle conducive to facilitate movement of the dispenser containing the ophthalmic medicament into engagement with the first dropper receiver.

12. The apparatus of claim 11 wherein the dispenser contains a solution comprising the ophthalmic medicament.

13. The apparatus of claim 11 wherein the dispenser contains an ophthalmic suspension comprising the ophthalmic medicament.

14. A method for administration of ophthalmic solutions into a patient's eyes, the method comprising:
placing an apparatus over the patient's eyes, the apparatus comprising:
a right upper frame and a left upper frame, the right upper frame and the left upper frame connected via a bridge comprising a formable frame expansion extending upward from the right upper frame and the left upper frame and through the bridge sufficiently to contact a forehead of a patient located above a brow of the patient while the right upper frame and the left upper frame are positioned over the brow of the patient, and to provide upper support of the right upper frame and the left upper frame;
a formable right nose pad and a formable left nose pad sized to rest upon a right nose side and a left nose side respectively of the patient to provide lower support of the right upper frame and the left upper frame while the right upper frame and the left upper frame are positioned over the brow of the patient;
a right temple extendable from the right upper frame over a right ear of the patient when the right upper frame is positioned over the brow of the patient;
a left temple extendable from the left upper frame over a left ear of the patient when the left upper frame is positioned over the brow of the patient;
a first dropper receiver supported by the right upper frame; and guide features fixedly attached to the first dropper receiver and extending outward from the first dropper receiver at an angle conducive to facilitate movement of a dispenser containing an ophthalmic medicament into engagement with the first dropper receiver; and
the right upper frame and the left upper frame supporting a distance measuring means and a signaling means, wherein the distance measuring means is functional to assess a distance of the first dropper receiver from a surface of the patient's eyes;
wherein,
the apparatus is formed from a contiguous item of wire frame;
the formable frame expansion further includes a left portion and a right portion; and
the contiguous item of wire frame extends from the formable right nose pad and through the bridge to form the left portion of the formable frame expansion, and further extends to form the right portion of the formable frame expansion opposite the left portion of the formable frame expansion, cross the bridge, and form the formable left nose pad;
placing the dispenser comprising the ophthalmic medicament into physical interaction with the guide features;
directing movement of the dispenser towards the first dropper receiver with the guide features;
moving the dispenser into engagement with the first dropper receiver;
supporting the dispenser above the patient's eyes at a distance conducive to an accurate placement of a drop of the ophthalmic medicament from the dispenser into the patient's eyes and preventing the dispenser from touching the patient's eyes; and
dispensing the drop of the ophthalmic medicament from the dispenser into a patient's eye while the dispenser is engaged by the first dropper receiver.

15. The method of claim 14, additionally comprising the step of fixedly attaching the guide features to the first dropper receiver, wherein a left focal element is further formed on the left portion of the formable frame expansion, and a right focal element is further formed on the right portion of the formable frame expansion.

16. The method of claim 14, additionally comprising the steps of removing the dispenser from engagement with the first dropper receiver and engaging the dispenser with a second dropper receiver and dispensing the drop of the ophthalmic medicament from the dispenser while the dispenser is engaged by the second dropper receiver.

17. The method of claim 14 wherein the apparatus comprises a plastic surface comprising the first dropper receiver.

18. The method of claim 15 wherein the guide features and the first or second dropper receiver are formed into a plastic surface, and the method additionally comprises the step of fixedly attaching the plastic surface to the right upper frame and the left upper frame.

\* \* \* \* \*